United States Patent [19]

Vaughan

[11] Patent Number: 4,545,783

[45] Date of Patent: Oct. 8, 1985

[54] RIGID MEDICAL SOLUTION CONTAINER

[75] Inventor: Thomas L. Vaughan, Valley Center, Calif.

[73] Assignee: Warner-Lambert Company, Morris Plains, N.J.

[21] Appl. No.: 512,817

[22] Filed: Jul. 11, 1983

[51] Int. Cl.⁴ ............................................. A61M 5/00
[52] U.S. Cl. .................................... 604/259; 604/251; 206/438; 206/364
[58] Field of Search ............... 604/132, 148, 183, 185, 604/212, 151–155, 259; 206/571, 572, 216, 438, 364

[56] References Cited

U.S. PATENT DOCUMENTS

| 1,766,724 | 6/1930 | Russow. | |
|---|---|---|---|
| 2,062,040 | 11/1936 | Rigney | 206/69 |
| 2,333,684 | 11/1943 | Schwab | 206/438 |
| 2,473,068 | 6/1949 | Nalpantian | 128/227 |
| 2,690,180 | 9/1954 | Leonard et al. | 128/227 |
| 2,851,035 | 9/1958 | Perry et al. | 206/438 |
| 2,861,718 | 11/1958 | Winzen | 222/107 |
| 3,006,341 | 10/1961 | Poitras | 128/214 |
| 3,100,487 | 8/1963 | Bathish | 128/227 |
| 3,311,268 | 11/1964 | Fields | 604/251 |
| 3,384,231 | 5/1968 | Cox | 206/69 |
| 3,690,315 | 9/1972 | Chittenden et al. | 604/324 |
| 3,904,060 | 9/1975 | McPhee | 604/403 |
| 4,278,085 | 6/1981 | Shim | 604/153 |
| 4,282,863 | 8/1981 | Beigler et al. | 128/1 R |
| 4,301,926 | 11/1981 | Chung | 206/620 |

Primary Examiner—C. Fred Rosenbaum
Assistant Examiner—Karen Kaechele
Attorney, Agent, or Firm—Neil K. Nydegger

[57] ABSTRACT

A container with attached tubing set, for use in the administration of fluids to a patient, comprises a reservoir in fluid communication with the tubing set and an enclosure integrally associated with the reservoir and adapted to coilably receive the tubing set when the container is not in use. The container further includes a seal over an opening to the enclosure which is removable to extend the tubing set, and provide a fluid path therethrough, from the reservoir to the patient during administration of the fluid.

5 Claims, 8 Drawing Figures

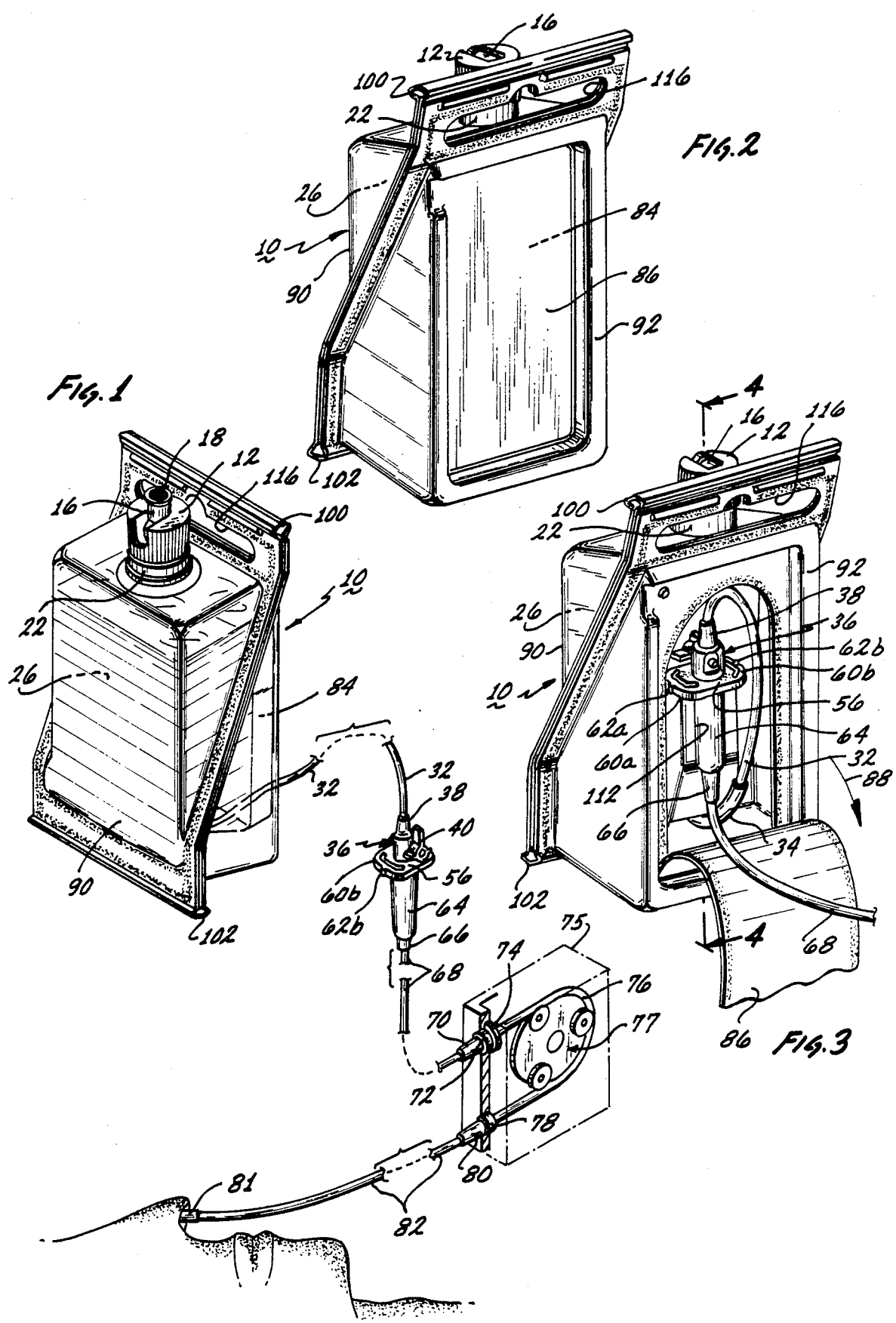

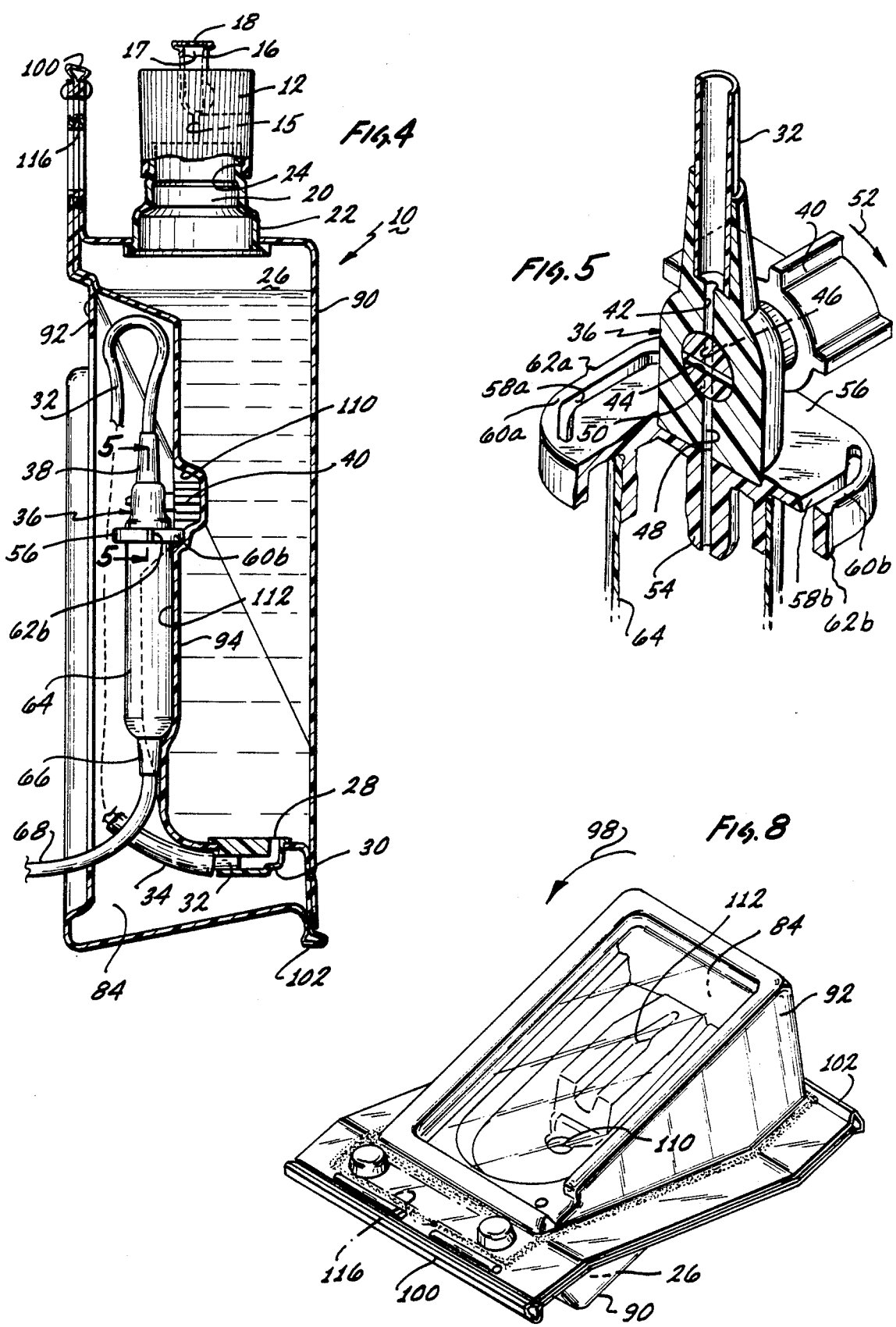

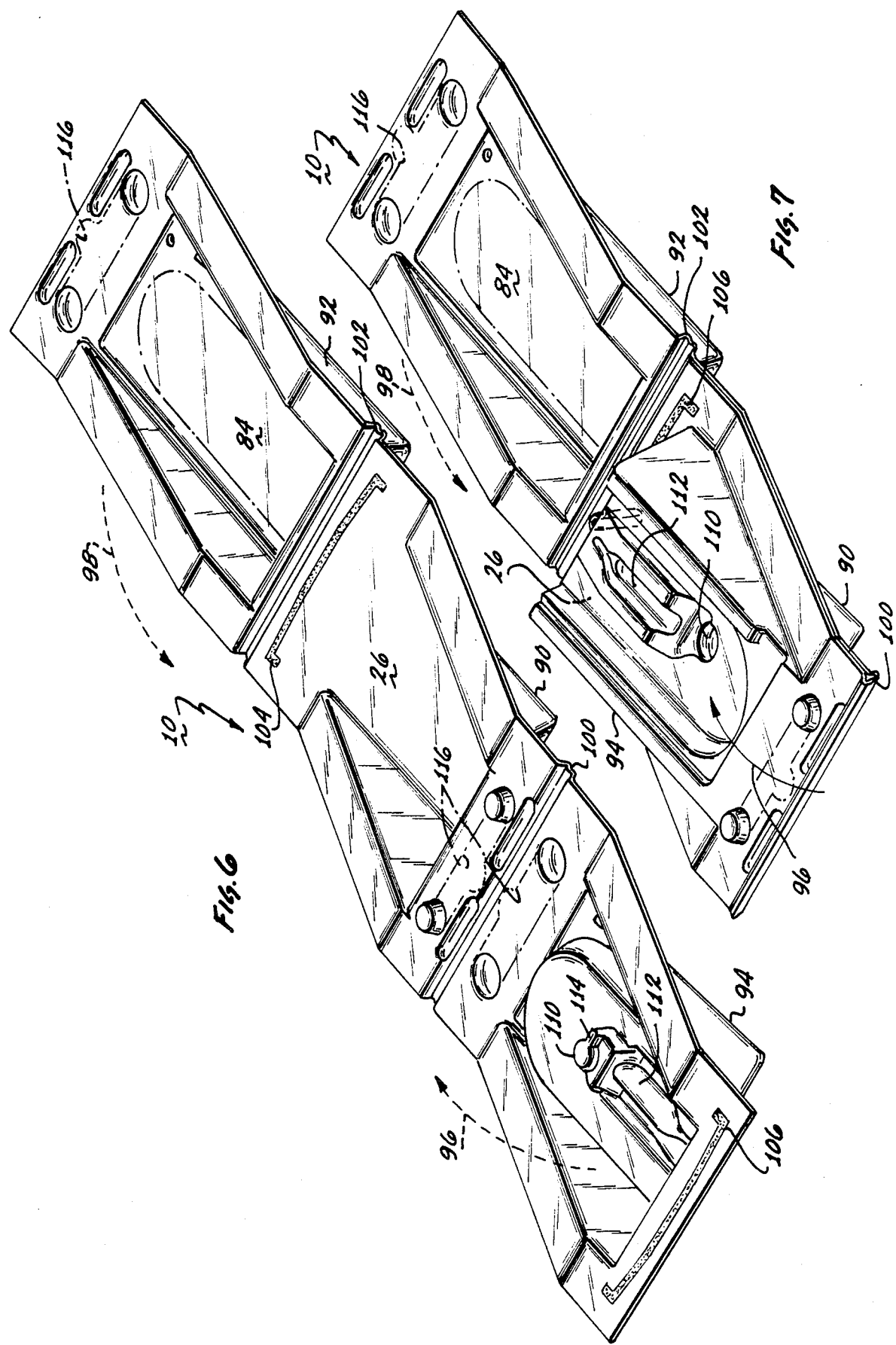

RIGID MEDICAL SOLUTION CONTAINER

BACKGROUND OF THE INVENTION

This invention relates generally to containers and associated apparatus for the dispensing of fluids. More particularly this invention relates to a container having a fluid reservoir and an associated separate enclosure for storing a tubing set which is in fluid communication with the reservoir. The present invention also provides the capability for operably connecting the tubing set with a pump to assist and control the flow of fluid from the reservoir through the tubing set. This invention is particularly, though not exclusively, useful in the parenteral or enteral administration of medical fluids or nutrients to a patient and for the administration of blood to a patient.

DESCRIPTION OF THE PRIOR ART

Containers to hold enteral or parenteral fluid solutions that are to be administered to patients come in many configurations which are well known in the pertinent art. For each configuration, however, the entire system must typically include the container in operative association with a delivery device, such as a tubing set, for transferring the solution in the container to the patient. In systems where the container and tubing set are provided separately, the containers need to incorporate fitments that are adapted to connect the container with the tubing set. With such a configuration, there is always the need to ensure both the availability of a separate tubing set and the compatibility of the particular tubing set with the particular container. In health care environments, this can consume time and reduce efficiency.

When enteral or parenteral solutions need to be prepared shortly before their administration to the patient, either because of their composition or due to their inability to withstand prolonged storage, there is a need for containers which are initially empty. Medical personnel or their associates are then confronted with the task of filling the container. The unfilled containers presently available are generally flexible and collapsible and of a type similar to the containers disclosed in U.S. Pat. No. 4,368,729 and U.S. Pat. No. 3,006,341. Such containers, because they are collapsible, are difficult to hold in a steady position during the filling process and, when filled, can be difficult to grasp or stack with other similarly filled containers.

Another requirement of containers used for the administration of medical solutions is the capability of being sterilized to keep the interior of the container free of contamination prior to the introduction of the solution into the container. This requirement is of particular importance when parenteral solutions are involved. Also, there is a concomitant need to keep the tubing set free of contamination until such time as the administration of the solution has been completed. Consequently, there is a need to provide as much protection from contamination for the container and its associated tubing set as is possible. Typically, in presently available medical fluid administation systems, the container and tubing set are attached together in a manner which protects only their interior portions from contamination. Furthermore, such freedom from contamination is not always achieved since the process of attaching the tubing set to the container can itself introduce contamination into the container and tubing set. Even if the attachment is made without contaminating their interiors, the exterior portions of the container and tubing set are exposed to contamination. Additionally, after attachment, the tubing set is generally extended and left to hang from the container. This not only increases the opportunities for contaminating the interior of the tubing set, it also makes the container and tubing set more difficult to manage and increases the possibility of entangling the tubing set before its use.

Some of the above mentioned needs are addressed separately, but not collectively, by the prior art. For example, U.S. Pat. No. 2,062,040 and U.S. Pat. No. 2,473,068 disclose containers having an integral enclosure for concealing or holding a fluid dispensing tube that is operatively associated with the fluid reservoir of the container. These patents do not, however, address a need for the container and associated tubing to be sterilizable. Further, these patents neither teach nor suggest the use of such a device in the medical field for the administration of enteral or parenteral solutions.

Athough the present invention can be used in any of the wide variety of tasks which require the storage and dispensing of fluids, the environment where its advantages promise to be the most pronounced is in the medical field. Accordingly, it is an object of the present invention to provide a semi-rigid container which can be easily filled, carried and used in a medical environment. A further object of the invention is to provide a sterilizable enclosure, integrally associated with the container for holding a tubing set until use of the tubing set is required. Still another object of the present invention is to provide a container which is easily stacked with other containers regardless whether the containers are empty or filled with a medical solution.

SUMMARY OF THE INVENTION

In a preferred embodiment of the present invention, a semi-rigid transparent container for holding medical solutions is provided with an integrally attached tubing set. Within the container there is a reservoir for holding fluids prior to their administration to a patient and an enclosure into which the tubing set can be placed when it is not in use.

Fluids are poured into the reservoir through a fill spout located at the top of the container. A cap for the fill spout having a flip-open vent with integral air filter is provided to prevent spillage of fluid from the reservoir. Presence of the air filter creates a bacterial seal with the flip-open vent in either the closed or the open position. When this vent is flipped to the open position, the reservoir is vented through the air filter and fluid in the reservoir can be drained. At the bottom of the reservoir on the interface surface between the reservoir and the enclosure is an output fitment which attaches the tubing set in fluid communication with the reservoir. A tear strip provides a bacterial seal and retains the tubing set within the enclosure until the tear strip is removed and the tubing set is extended for operation.

Also included in the present invention is a valved drip chamber that is incorporated into the tubing set. An important feature of this drip chamber is the stop cock which is directly associated with the top of the drip chamber. During filling of the reservoir and subsequent preparation of the container for administering the fluids, this valve remains closed. Once the tubing set is removed from the enclosure, the location of the valve on top of the drip chamber allows for convenient manipulation of the valve to permit fluid flow through the tubing set.

In an alternate embodiment of the present invention, a section of silicone rubber tubing can be added to the tubing set. This section of tubing is particularly effective for operative association with a peristaltic pumping device which will assist in the transfer of fluid from the reservoir through the tubing set and on to the patient.

The novel features of this invention, as well as the invention itself, both as to its organization and operation will best be understood from the accompanying drawings, taken in conjunction with the accompanying description, in which reference characters refer to similar parts, and in which:

BRIEF DESCRIPTION OF THE DRAWINGS

FIG. 1 is a perspective view of the container and tubing set shown in conjunction with a peristaltic pump as employed for the delivery of fluid to a patient;

FIG. 2 is a perspective view of the back of the invention;

FIG. 3 is a perspective view of the invention with the tear strip opened to expose the interior of the container for clarification and illustration;

FIG. 4 is a vertical sectional view taken along the line 4—4 of FIG. 3;

FIG. 5 is a perspective cross-sectional view of the top of the drip chamber used in the preferred embodiment of this invention;

FIG. 6 is a perspective view of the unassembled container;

FIG. 7 is a view similar to FIG. 6 but showing a partial assembly of the container; and FIG. 8 is a view similar to FIG. 7 but showing the container in an assembled configuration.

DESCRIPTION OF THE PREFERRED EMBODIMENT

Referring initially to FIG. 1, it is seen that the preferred embodiment of the invention includes a carton generally designated 10. Also seen in FIG. 1 is a cap 12 which has a flip-open vent 16 pivotally associated therewith. As seen in both FIG. 1 and FIG. 4, the vent 16 is in the open position. As seen in FIG. 2 and FIG. 3, the vent 16 is in the closed position. As is best seen in FIG. 4, the vent 16 has an air passage 17 therethrough and a filter element 18 operatively disposed in the air passage 17 near the outer end of vent 16. Also seen in FIG. 4 is an air passage 15 that is formed into cap 12 to provide for air communication between reservoir 26 and the environment when vent 16 is in the open position.

As can be best seen in FIG. 4, the carton 10 is provided with a fill spout 20 which is defined by fill spout flange 22. Fill spout flange 22 is attached to carton 10 by any manner well known in the pertinent art, such as by radio frequency welding. In order to cooperate with cap 12, fill spout flange 22 is formed with threads 24 which threadably engage cap 12 in a manner that permits the cap 12 to be either operatively associated with the carton 10 or disengaged from the flange 22 and removed from carton 10 to provide an open passageway at fill spout 20 through which medical solutions can be poured into reservoir 26. As shown in FIG. 4, the reservoir 26 is formed within carton 10.

Still referring to FIG. 4, it is seen that reservoir 26 is provided with an output port 28. An output fitment 30 is operatively associated with reservoir 26 by a connection which provides for fluid communication through output port 28. Output fitment 30 is rigidly attached to reservoir 26 at output port 28 by any means well known in the art, such as by radio frequency welding. Also, output fitment 30 is adapted for attachment to a tubing section 32 by means well known in the art, such as by solvent bonding. Preferably, the tubing section is made of polyvinyl chloride (PVC). A sleeve 34 of macrobore tubing which may be made of polyvinyl chloride is slidably disposed over tubing section 32 in order to protect tubing section 32 from crimping.

The end of tubing section 32 opposite from the end which was joined to output fitment 30 is joined to the extension 38 of drip chamber top 36 by a means well known in the art, such as by solvent bonding. As can be best seen with reference to FIG. 5, drip chamber top 36 is formed with a cannula 54 and is operatively associated with a valve 50. Drip chamber top 36 is also formed with an upper passage 42 and a lower passage 48. Valve 50 is formed with a valve passage 44 and is rigidly attached to valve handle 40 so that upon rotation of valve handle 40 in the direction of arrow 52, the valve passage 44, as shown in FIG. 5, is moved into a position shown in phantom as 46. When valve handle 40 has been rotated so that passage 44 is in the position 46, fluid communication between tubing set 32 and cannula 54 is accomplished. An engagement flange 56 is rigidly attached to drip chamber top 36. Contraposed slots 58a and 58b are formed into engagement flange 56 to respectively define springs 60a and 60b. Formed onto springs 60a and 60b are the protrusions 62a and 62b. As formed in this manner, engagement flange 56 can be operatively associated with a drop sensor (not shown) such as the type described in U.S. Pat. Nos. 4,346,606 and 4,300,552.

The bell shaped portion of drip chamber 64 is preferably made from a flexible polyvinyl chloride (PVC) and is disposed around the cannula 54 of engagement flange 56. The bell shaped portion of drip chamber 64 is attached to the engagement flange 56 by radio frequency welding or by any other means well known in the art. A connector 66 is formed at the end of drip chamber 64 opposite from the end where drip chamber 64 is attached to engagement flange 56. Connector 66 is bonded to tubing section 68 by means known in the art such as by solvent bonding.

Tubing section 68, which like tubing section 32 is preferably made of polyvinyl chloride, extends from the connector 66 of drip chamber 64 and is solvent bonded to an input connector 70. The input connector 70 has a fluid passageway (not shown) therethrough and is formed with an input collar 72. As can be seen in FIG. 1, a ring 74 is formed onto input collar 72. With this structure, ring 74 and input collar 72 can be operatively associated with a retainer slot (not shown) in a peristaltic pump (not shown). As shown in FIG. 1, for illustrative purposes only, a portion of a peristaltic pump has been indicated for incorporation into the system by the representative block 75. Attached to input collar 72 on a side opposite from input connector 70 is one end of a rubber tubing 76 which is disposed in operative contact with a peristaltic roller assembly shown generally at 77. Rubber tubing 76 is preferably made of a material, such as silicone rubber, which is well known in the art as being suited for operation in a peristaltic action. The other end of rubber tubing 76 is attached to an output connector 80 having a fluid passageway (not shown) therethrough. Output connector 80 is formed with an output collar 78 and output collar 78 is held into the block 75, which represents a peristaltic pump, by a retainer slot (not shown). At this point it should be recognized that the ring 74 makes input collar 72 a different size than the output collar 78. Both input collar 72 and output collar 78 are preferably made with polyethylene, and their difference in size a well as the difference in size of their respective retainer slots (not shown) allow for placement of the rubber tubing 76 into the peristaltic pump, represented by block 75, only in the direction which results in fluid flow from the reservoir 26 and to the patient during operation of the peristaltic pump represented by block 75.

Output connector 80 provides means for attachment with tubing section 82. This connection is accomplished by any manner well known in the art, such as by solvent bonding. Tubing section 82 is then connected to a patient's nasogastric fitment (not shown) which in turn is attached to the patient's nasogastric or jejuneostimy tube neither of which are shown in detail but which are shown in general configuration by the reference character 81 in FIG. 1.

Turning again to FIG. 4, it can be seen that the carton 10 is divided into a reservoir 26 and an enclosure 84 by the interdivider panel 94. As can be further appreciated by reference to FIG. 4, enclosure 84 is adapted to coilably receive the drip chamber 64 together with tubing section 32, tubing section 68, rubber tubing 76, and tubing section 82 and their associated connectors.

As is best shown in FIG. 6 and FIG. 7, the interdivider panel 94 is formed with a drip chamber nest 112, a valve nest 110, and a valve handle nest 114. When placed into enclosure 84 for storage, drip chamber 64 is placed into drip chamber nest 112. As formed into interdivider panel 94, the valve nest 110 and valve handle nest 114 are adapted to receive valve handle 40 in a manner which ensures that the valve passage 44, and thus valve 50, are in the closed position as shown in FIG. 5. As thus described, the drip chamber 64 and the assorted tubing sections of the present invention can be held within enclosure 84 by a tear strip 86. Tear strip 86 is preferably an adhesive coated gas permeable Tyvek paper, such as the type manufactured by Oliver Products Company, which is heat sealed into position as shown in FIG. 2 to provide a bacterial seal for the enclosure 84.

FIG. 3 shows that the tear strip 86 can be removed from carton 10 to expose enclosure 84 by grabbing a corner of the tear strip 86 and rotating it in a direction shown by the arrow 88. This brings tear strip 86 into an open position as shown in FIG. 3 for exposure of the contents held in enclosure 84.

Referring now to FIG. 6, it can be appreciated that the carton 10 is initially thermoformed from a single sheet of a semi-rigid transparent plastic, preferably from 25 ml PETg (polyethylene teripheilate, glycoal modified). As shown in FIG. 6, the carton 10 comprises a front panel 90, a back panel 92, and an interdivider panel 94. As will become apparent in the further description of the preferred embodiment, the front panel 90 is thermoformed intermediate the back panel 92 and interdivider panel 94. Also formed into the carton 10 is a fold hinge 100 connecting interdivider panel 94 with front panel 90 and fold hinge 102 connecting front panel 90 with back panel 92. During construction of the carton 10, the interdivider panel 94 is rotated about the fold hinge 100 in a direction indicated by the arrow 96 to bring interdivider panel 94 into contact with the front panel 90, and weld line 106 is aligned with weld line 104. It can be appreciated that this connection forms the reservoir 26. In this position interdivider panel 94 is attached to front panel 90 at the junction of weld line 104 and weld line 106 in a manner well known in the art, such as by heat sealing or radio frequency welding.

The next step in construction of the carton 10 requires the rotation of back panel 92 about the fold hinge 102 in the direction of the arrow 98 as shown in FIG. 8. This operation brings back panel 92 into contact with interdivider panel 94 for defining the enclosure 84. With the carton 10 now interconnected as shown in FIG. 8, the front panel 90, the back panel 92, and the interdivider panel 94 are sealed together along the weld line 108 as shown in FIG. 8 in any manner well known in the art such as by heat sealing or radio frequency welding.

OPERATION

In operation, the carton 10 is assembled with drip chamber 64 placed into the enclosure 84 and fitted into drip chamber nest 112. The valve handle 40 associated with drip chamber 64 is also placed into enclosure 84 and is oriented with respect to drip chamber 64 so as to fit into valve nest 110 and valve handle nest 114. As is seen in FIG. 5 with valve handle 40 in the above described orientation, the valve 50 is closed, thus, valve passage 44 is not aligned with the upper passage 42 and the lower passage 48, and there is no fluid communication between tubing section 32 and the drip chamber 64. Also placed into the enclosure 84 are tubing sections 32 and 68, rubber tubing 78, and tubing section 82. These sections are placed into enclosure 84 in any suitable manner, such as by coiling around the drip chamber 64. Tear strip 86 is heat sealed onto carton 10 in such a manner that the drip chamber 64 and the associated tubing sections are held in enclosure 84 until carton 10 is ready to be placed into operation.

For gas sterilization of the rigid medical solutions carton 10, cap 12 is threadably engaged to fill spout flange 22 and vent 16 is rotated to the open position for air communication between the reservoir 26 and the ambient atmosphere through filter element 18. Use of a gas permeable paper for tear strip 86 allows for the gas sterilization of carton 10 in the above described orientation. Carton 10 can now be gas sterilized. After gas sterilization the vent 16 is rotated into the closed position. It should also be understood that carton 10 can be radiation sterilized. In the latter case there is no real need for the vent 16 to be in the open position.

Due to the closed configuration of carton 10, filling of the reservoir 26 can be accomplished by removal of the cap 12 from carton 10. This exposes fill spout 20 for the introduction of fluids into the reservoir 26. After the medical solutions or fluids have been introduced into the reservoir 26, the cap 12 with vent 16 in the closed position is again threadably engaged with fill spout flange 22. The carton 10 can now be stacked or carried by use of a handle 116 which has been formed into the carton 10. Carton 10 is ready for use in the administration of medical solutions contained in reservoir 26.

For the administration of medical solutions, the carton 10 is prepared by removing the tear strip 86 from the back of carton 10. This exposes the drip chamber 64 and the associated tubing sections. Carton 10 can be suspended from an IV pole (not shown) or any other convenient structure which is available for use. Rubber tubing 76 is now placed into operative association with a peristaltic pump, such as the one represented in FIG. 1 by block 75. This is accomplished by fitting the input collar 72 and output collar 78 into retainer slots (not shown) on the peristaltic pump representatively shown as block 75. Rubber tubing 76 is then operatively associated with the peristaltic roller assembly generally shown as 77 in FIG. 1. Tubing section 82 is then joined with the nasogastric fitment 81. Vent 16 is rotated to the open position to provide air passage through the vent 16 and through the filter element 18 disposed therein. Fluid passage from the reservoir 26 through tubing section 32 and through chamber 64 is accomplished by rotation of valve handle 40 in the direction of arrow 52 to align the valve passage 44 into the position 46 shown in FIG. 5 and allow fluid communication between the upper passage 42 and the lower passage 48. Drip chamber 64 can be pinched by the operator to allow the partial accumulation of fluid within drip chamber 64. The peristaltic pump represented by block 75 can now be adjusted for the controlled pumping of medical solutions through the rubber tubing section 76.

It must be understood that disclosure of the peristaltic pump represented by block 75 was for illustrative purposes only. In an alternate embodiment of the present invention, there is no need for the structure described herein for operative association with block 75. Indeed an embodiment wherein rubber tubing 76, input connector 70, input collar 72, ring 74, output collar 78 and output connector 80 are omitted is also operational as a gravity device. On the other hand, it must also be understood that pumps other than a peristaltic pump can be used in combination with the present invention. For example, an IV pump as disclosed in U.S. Pat. No. 3,985,133 may be used.

While the particular rigid medical solution container and associated tubing set as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the apended claims.

I claim:

1. A gas sterilizable container for use in the administration of a medical solution to a patient which comprises:
    a reservoir, formed with a fill spout and an output port, for holding the medical solution;
    a tubing set, forming a fluid passageway, attached in fluid communication to said output port for conveying the medical solution from said reservoir to the patient;
    a drip chamber having a stop cock type valve disposed in the fluid passageway for permitting fluid flow therethrough;
    a cap removably associated with said fill spout having a filtered vent rotatable between an open position wherein said reservoir is vented and a closed position wherein fluid flow through said cap is prevented;
    an enclosure integrally attached to said reservoir and having an opening adapted to coilably receive said tubing set within said enclosure; and
    a gas permeable tear strip removably attached to said container to form a bacterial seal over the opening of said enclosure and hold said tubing set in said enclosure.

2. A container as cited in claim 1 wherein said reservoir and said enclosure are made of a semi-rigid transparent material.

3. A container as cited in claim 2 which further comprises means on said tubing set operatively engagable with a fluid pump for assisting the flow of medical solution from said reservoir to the patient through said tubing set.

4. A sterilizable container for use in the administration of a medical solution to a patient which comprises:
    a semi-rigid carton formed with a reservoir and an enclosure, said reservoir having a fill spout and an output port, and said enclosure having an opening is disposed in a surrounding relationship to said output port;
    a cap having an air passage therethrough removably associated with said fill spout;
    a filtered vent, to provide a bacterial seal, operatively associated with said cap for rotation between an open position to allow air communication between said reservoir and said vent via said air passage and a closed position to prevent fluid communication between said reservoir and said vent through said air passage;
    a tubing set, adapted to be coilably received in said enclosure and removed therefrom, attached in fluid communication with said output port for conveying the medical solution from said reservoir to the patient;
    a drip chamber having an integral valve for controlling fluid flow therethrough; and
    a gas permeable tear strip removably attached to said container to form a bacterial seal over the opening of said enclosure for holding said tubing set in said enclosure.

5. A container as cited in claim 4 which further comprises means for operatively engaging said tubing set with a fluid pump to assist the flow of medical solution therethrough.

* * * * *